US008735629B2

(12) United States Patent
Laven et al.

(10) Patent No.: US 8,735,629 B2
(45) Date of Patent: May 27, 2014

(54) PROCESS FOR THE REDUCTION OF A TERTIARY PHOSPHINE OXIDE TO THE CORRESPONDING TERTIARY PHOSPHINE IN THE PRESENCE OF A CATALYST AND USE OF A TERTIARY PHOSPHINE FOR REDUCING A TERTIARY PHOSPHINE OXIDE IN THE PRESENCE OF A CATALYST

(75) Inventors: Gaston Laven, Stockholm (SE); Martin Kullberg, Sollentuna (SE)

(73) Assignee: Chromafora AB, Nacka (SE)

( * ) Notice: Subject to any disclaimer, the term of this patent is extended or adjusted under 35 U.S.C. 154(b) by 38 days.

(21) Appl. No.: 13/636,152

(22) PCT Filed: Mar. 29, 2011

(86) PCT No.: PCT/SE2011/050355
§ 371 (c)(1),
(2), (4) Date: Sep. 20, 2012

(87) PCT Pub. No.: WO2011/123037
PCT Pub. Date: Oct. 6, 2011

(65) Prior Publication Data
US 2013/0012725 A1    Jan. 10, 2013

Related U.S. Application Data

(60) Provisional application No. 61/387,697, filed on Sep. 29, 2010.

(30) Foreign Application Priority Data

Mar. 31, 2010  (SE) ........................................ 1050311

(51) Int. Cl.
*C07F 9/53*  (2006.01)

(52) U.S. Cl.
USPC ................................... 568/14; 568/8; 568/16

(58) Field of Classification Search
USPC .......................................... 568/8, 14, 16, 17
See application file for complete search history.

(56) References Cited

U.S. PATENT DOCUMENTS

| 4,113,783 A | 9/1978 | Malpass et al. |
| 4,507,504 A | 3/1985 | Lee et al. |
| 4,727,193 A * | 2/1988 | Dockner ........................... 568/8 |
| 5,693,868 A * | 12/1997 | Sayo et al. ........................ 568/8 |
| 6,333,291 B1 * | 12/2001 | Yokozawa et al. ............. 502/162 |
| 7,491,779 B2 | 2/2009 | Steinke et al. |

FOREIGN PATENT DOCUMENTS

WO    WO 2010/012096 A1    2/2010

OTHER PUBLICATIONS

Brown et al; Journal of Chemical Society Chemical Communications, 1977, 708-709.*
Zhang et al; Journal of Organic Chemistry, 2001, 66, 327-329.*
Field et al; Tetrahedron Letters, 38, 1997, 2779-2782.*
Bollmark et al; Chemical Communications, 2001, 771-772.*
Olah et al; Journal of Organic Chemistry, 1978, 43, 4503-4505.*
Krawczyk et al; Journal of Organic Chemistry, 1992, 57, 4963-4970.*
Brock et al; Inorganic Chemistry, 1991, 30, 2138-2143.*
Jung et al; Angewandte Chemie International Edition in English, 1996, 35, 17-42.*
International search report dated Jul. 6, 2011 in corresponding PCT/SE2011/050355.
Kullberg M. et al., "Theoretical investigations on the mechanism of chalcogens exchange reaction between P(V) and P(III) compounds", Journal of Organometallic Chemistry, Elsevier-Sequoia S.A. Lausanne, CH, vol. 609, No. 10, May 16, 2005, pp. 2571-2576, XP004877394.
Yano T. et al., "Electroreduction of triphenylphosphine dichloride and the efficient one-pot reductive conversion of phosphine oxide to triphenylphosphine", Tetrahedron Letters, Elsevier, Amsterdam, NL, vol. 51, No. 4, Jan. 27, 2010, pp. 698-701, XP026815299.
Hai-Chen Wu et al., "Stereospecific Deoxygenation of Phosphine Oxides with Retention of Configuration Using Triphenylphosphine or Triethyl Phosphite as an Oxygen Acceptor", Department of Chemistry, Cambridge University, Cambridge CB2 1 EW, United Kingdom, Sep. 2, 2004, Organic Letters, pp. 4675-4678.
Ying-Hao Liu et al., "Asymmetric Aza-Morita-Baylis-Hillman Reaction of N-Sulfonated Imines with Activated Olefins Catalyzed by Chiral Phosphine Lewis Bases Bearing Multiple Phenol Groups", State Key Laboratory of Organometallic Chemistry, Shanghai Institute of Organic Chemistry, Chinese Academy of Sciences, 354 Fenglin Lu, Shanghai 200032, People's Republic of China, Received: Dec. 15, 2005; Accepted: Mar. 2, 2006, pp. 973-985.

* cited by examiner

*Primary Examiner* — Sudhakar Katakam
*Assistant Examiner* — Pancham Bakshi
(74) *Attorney, Agent, or Firm* — Young & Thompson

(57)  ABSTRACT

A process for the conversion of a tertiary phosphine oxide to the corresponding tertiary phosphine includes reacting the tertiary phosphine oxide with a reducing tertiary phosphine, in the presence of a catalyst that catalyzes the conversion.

19 Claims, No Drawings

PROCESS FOR THE REDUCTION OF A TERTIARY PHOSPHINE OXIDE TO THE CORRESPONDING TERTIARY PHOSPHINE IN THE PRESENCE OF A CATALYST AND USE OF A TERTIARY PHOSPHINE FOR REDUCING A TERTIARY PHOSPHINE OXIDE IN THE PRESENCE OF A CATALYST

TECHNICAL FIELD

The present invention relates to a process for producing tertiary phosphines. More particularly, the invention relates to a process for producing a tertiary phosphine by reduction of the corresponding tertiary phosphine oxide.

TECHNICAL BACKGROUND

Phosphines, the phosphorous analogues of organic amines, constitute a class of highly important compounds with widespread industrial applicability within numerous areas. Tertiary phosphines are involved in a variety of extensively utilized chemical reactions, for instance the Wittig reaction, i.e. the conversion of a ketone or an aldehyde functionality into an olefin linkage, the Mitsunobu reaction for stereo-specific preparations of C—O, C—N, C—S, or C—C bonds from alcohol functionalities, the Staudinger reaction, i. e. conversion of azides to free amides, or the Apple reaction for stereo-specific transformation of alcohols to halides. Additionally, phosphines are utilized as ligands in homogenous catalysis.

Tertiary phosphines are commonly prepared through reduction of the corresponding phosphine oxides. Over the years, concomitantly with the realization that tertiary phosphines are highly versatile and useful compounds for various applications, numerous different processes for the preparation of these organophosphorous agents have been developed. However, virtually all chemical processes for preparing tertiary phosphines suffer from one or more disadvantages, relating to for instance cost, reagent handling, high reaction temperature intervals, severe purification requirements, or significant environmental impact, as well as the inherent complexity of the reaction system. Polymeric analogues of triphenyl-phosphine have, inter alia, been reported as a means to mitigate the problem with extensive purification, enabling simple filtration-based removal of the undesired product of a particular chemical reaction. However, despite being an elegant solution to the purification problem, issues associated with high reagent cost and substantial water requirements decrease the utility of said strategy.

An alternative approach for allegedly generating a relatively pure tertiary phosphine product, supposedly obtainable through an economically feasible route, is disclosed in U.S. Pat. No. 4,113,783, wherein triphenylphosphine oxide is reacted with a dialkylaluminium hydride followed by subsequent hydrolysis, in order to obtain the desired product. A similar approach is disclosed in U.S. Pat. No. 4,507,504, where the reducing agent is a trialkylaluminium/boron trihalide compound, again providing a purportedly inexpensive route to tertiary phosphines. Despite disclosing asserted inexpensive routes to tertiary phosphines, the environmental impact of essentially all tertiary phosphine producing reactions of the prior art is very high, inter alia as a result of the use of harsh reagents, high temperatures, and/or substantial amounts of solvents. Further, numerous teachings of the prior art relate to procedures with low susceptibility for industrial application, relatively often as an implication of a lack of scalability, or as a result of the use of harsh reagents, obstructing safe and environmentally feasible process development.

SUMMARY OF THE INVENTION

There is thus a significant need in the art for improved processes for conversion of tertiary phosphine oxides into the corresponding tertiary phosphines, with desired characteristics such as for instance inexpensiveness, simplicity, scalability, ease of handling, and efficiency, as well as low environmental impact.

Bearing in mind the substantial drawbacks associated with the processes constituting state-of-the-art, it is an object of the present invention to overcome said drawbacks and to satisfy the existing needs, by providing an inexpensive, simple, and highly efficient chemical process with minimal environmental impact.

According to a first aspect the present invention therefore pertains to an optimized process for converting tertiary phosphine oxides into the corresponding tertiary phosphines, utilizing a completely novel approach to the phosphine oxide reduction.

Thus, the present invention relates to a process for converting a tertiary phosphine oxide to the corresponding tertiary phosphine, comprising reacting said tertiary phosphine oxide with a reducing tertiary phosphine, in the presence of a catalyst, in order to obtain the desired corresponding tertiary phosphine from the tertiary phosphine oxide. Further, the invention pertains to numerous embodiments related to said conversion process, as well as to various uses for this highly efficient, simple, environmentally friendly, and scalable process.

In one embodiment, the process according to the invention may be represented by the following reaction scheme, wherein a tertiary phosphine oxide of formula (I) is reduced to the corresponding tertiary phosphine of formula (III) by reaction with a reducing tertiary phosphine (II) in the presence of a catalyst:

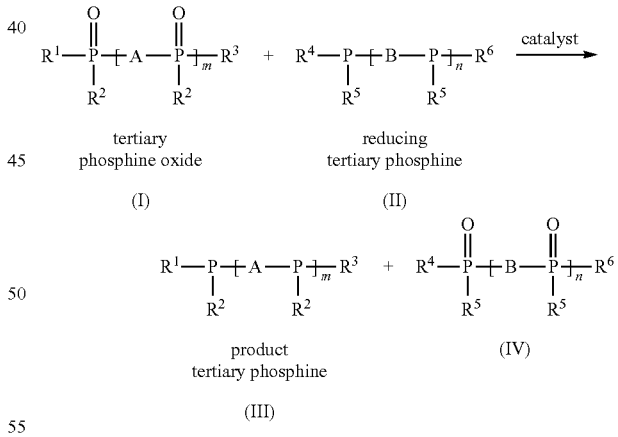

wherein
$R^1$, $R^2$ and $R^3$ are each independently selected from the group comprising substituted or unsubstituted, branched or linear hydrocarbyl; and substituted or unsubstituted carbocyclyl or heterocyclyl;
A is a linking moiety;
m is an integer of 0 to 2;
$R^4$, $R^5$ and $R^6$ are each independently selected from the group comprising substituted or unsubstituted, branched or linear hydrocarbyl; and substituted or unsubstituted carbocyclyl or heterocyclyl;

B is a linking moiety; and n is an integer of from 0 to 2.

The process of the present invention may very advantageously be used for reducing any tertiary phosphine oxide to the corresponding tertiary phosphine.

Furthermore, either the tertiary phosphine oxide to be reduced or the reducing tertiary phosphine may be attached to a solid support. In the first case, the process may be used for in situ generation of a tertiary phosphine from the corresponding tertiary phosphine oxide.

Thus, the present invention also provides a method of reducing a tertiary phosphine oxide attached to a solid support by bringing said tertiary phosphine oxide in contact with a reducing tertiary phosphine in the presence of a catalyst for the reaction.

In one aspect, the present invention relates to the use of a tertiary phosphine for reducing a tertiary phosphine oxide, by reacting said tertiary phosphine oxide with the tertiary phosphine in the presence of a catalyst.

The tertiary phosphine to be used as a reduction agent may be attached to a solid support. Thus, the present invention also provides a method of reducing a tertiary phosphine oxide by bringing said tertiary phosphine oxide in contact with a reducing tertiary phosphine attached to a solid support, in the presence of a catalyst.

Further aspects of the invention and embodiments thereof will be apparent from the following detailed description and the appended claims.

DETAILED DESCRIPTION OF THE INVENTION

Some terms used with respect to the present invention will first of all be defined.

Hydrocarbyl

The term "hydrocarbyl" as used herein refers to a moiety consisting exclusively of carbon and hydrogen atoms. As defined herein, the hydrocarbyl moiety is branched or linear and is aliphatic. The hydrocarbyl moiety may contain one or several unsaturations, i.e. one or several double bonds or one or several triple bonds, or both. The moiety may comprise 1, 2, 3, 4, 5, 6, 7, 8, 9, 10, 11, 12, 13, 14, 15, 16, 17, 18, 19 or 20 carbon atoms, such as 1 to 10 carbon atoms or 1 to 6 carbon atoms.

A substituted hydrocarbyl may carry one or several independently selected substituents and any substituent that does not interfere with the reduction reaction is considered as possible for the purpose of the present invention. It is considered that the person of ordinary skill in the art will be able to ascertain the suitability of a substituent without undue burden. For example, any substituent may be independently selected from substituted or unsubstituted carbocyclyl, substituted or unsubstituted heterocyclyl, halogen, hydroxy, thio, alkylthio, e.g. $C_1$-$C_{10}$ alkylthio, alkoxy, e.g. $C_1$-$C_{10}$ alkoxy, cyano, haloalkyl, etc.

Carbocyclyl

The term "carbocyclyl" as used herein refers to a cyclic moiety consisting exclusively of carbon and hydrogen atoms. As defined herein, the carbocyclyl moiety may be aliphatic or aromatic and monocyclic or polycyclic, e.g. bicyclic, tricyclic or tetracyclic, including bridged or fused cycles, as well as spiro cycles. An aliphatic carbocyclyl may contain one or several unsaturations, i.e. one or several double bonds or one or several triple bonds, or both. The moiety may comprise 3, 4, 5, 6, 7, 8, 9, 10, 11, 12, 13, 14, 15, 16, 17, 18, 19 or 20 carbon atoms. For example, the hydrocarbyl moiety may be polycyclic and contain e.g. 10 to 20 carbon atoms or monocyclic and contain e.g. 3 to 8 carbon atoms. Examples of carbocyclyl are cyclopropyl, cyclobutyl, cyclopentyl, cyclopentenyl, cyclopentadienyl, cyclohexyl, cyclohexenyl, cyclohexadienyl, norbornyl, bicyclo[2.2.2]octyl, phenyl, naphthyl, fluorenyl, azulenyl, indanyl, indenyl, anthryl etc.

A substituted carbocyclyl may carry one or several independently selected substituents and again it is considered that any substituent that does not interfere with the reduction reaction is possible, and that the person of ordinary skill in the art will be well able to ascertain the suitability of the substitution without undue burden, e.g. by following the general procedure described herein for reduction of the tertiary phosphine oxide into the corresponding tertiary phosphine, and by usual analytical techniques to ascertain the product identity and the product yield. For example, any substituent may be independently selected from substituted or unsubstituted hydrocarbyl, carbocyclyl or heterocyclyl, halogen, hydroxy, thio, alkylthio, e.g. $C_1$-$C_{10}$ alkylthio, alkoxy, e.g. $C_1$-$C_{10}$ alkoxy, cyano, haloalkyl, etc.

Heterocyclyl

The term "heterocyclyl" as used herein refers to a monocyclic or polycyclic, e.g. bi-, tri- or tetracyclic radical having 3, 4, 5, 6, 7, 8, 9, 10, 11, 12, 13, 14, 15, 16, 17, 18, 19 or 20 ring atoms, at least one of which, e.g. 1, 2, 3 or 4, such as 1 or 2, is a heteroatom selected from nitrogen, oxygen, phosphorus, silicon and sulphur, e.g. nitrogen, oxygen and sulphur. The cyclic radical may contain one or several unsaturations, i.e. one or several double bonds or one or several triple bonds, or both. Examples of heterocyclyl are pyridyl, pyrrolyl, quinolinyl, furyl, thienyl, oxadiazolyl, thiadiazolyl, thiazolyl, oxazolyl, pyrazolyl, triazolyl, tetrazolyl, tetrahydroquinolinyl, tetrazolyl, thiadiazolyl, thiazolyl, thiochromanyl, triazolyl, isoxazolyl, isothiazolyl, isoquinolinyl, naphthyridinyl, imidazolyl, pyrimidinyl, phthalazinyl, indolyl, pyrazolyl, pyridazinyl, pyrimidinyl, pyrrolyl, quinazolinyl, quinolinyl, quinolizinyl, quinoxalinyl, tetrahydroisoquinolinyl, pyrazinyl, indazolyl, indolinyl, indolyl, pyrimidinyl, thiophenetyl, pyranyl, chromanyl, cinnolinyl, quinolinyl, benzimidazolyl, benzodioxanyl, benzodioxepinyl, benzodioxolyl, benzofuryl, benzothiazolyl, benzoxadiazolyl, benzothiazolyl, benzoxazinyl, benzoxazolyl, benzimidazolyl, benzomorpholinyl, xanthenyl, phenoxathiinyl, phenazinyl, carbazolyl, acridinyl, carbolinyl, phenoxazinyl, benzoselenadiazolyl, benzothienyl, purinyl, cinnolinyl, pteridinyl, aziridinyl, phenantridinyl, azetidinyl, dihydropyranyl, dihydropyridyl, dihydropyrrolyl, dioxolanyl, dioxanyl, dithianyl, dithiolanyl, imidazolidinyl, imidazolinyl, morpholinyl, oxetanyl, oxiranyl, pyrrolidinyl, pyrrolidinonyl, piperidyl, piperazinyl, piperidinyl, pyranyl, pyrazolidinyl, quinuclidinyl, sulfalonyl, 3-sulfolenyl, tetrahydrofuryl, tetrahydropyranyl, tetrahydropyridyl, thietanyl, thiiranyl, thiolanyl, thiomorpholinyl, trithianyl, tropanyl etc.

A substituted heterocyclyl may carry one or several independently selected substituents and again it is considered that any substituent that does not interfere with the reduction reaction is possible, and that the person of ordinary skill in the art will be well able to ascertain the suitability of the substitution without undue burden. For example, any substituent may be independently selected from substituted or unsubstituted hydrocarbyl, carbocyclyl or heterocyclyl, halogen, hydroxy, thio, alkylthio, e.g. $C_1$-$C_{10}$ alkylthio, alkoxy, e.g. $C_1$-$C_{10}$ alkoxy, cyano, haloalkyl, etc.

Halogen

The terms "halogen" or "halo" etc, as used herein refer, to F, Cl, Br and I.

Alkyl

The term "alkyl", as used herein, refers to a hydrocarbyl radical. In case the alkyl is saturated, it is a radical according to the formula $C_nH_{2n-1}$, and then is referred to as a "$C_n$ alkyl".

Further, it should be understood that a moiety such as "$C_3$-$C_{20}$ cycloalkyl-$C_0$ alkyl" or "$C_6$-$C_{20}$ aryl-$C_0$ alkyl" represents a "$C_3$-$C_{20}$ cycloalkyl" and "$C_6$-$C_{20}$ aryl", respectively.

As defined herein, the alkyl also may be unsaturated (i.e. alkenyl or alkynyl), in which case it may contain one or several double bonds or one or several triple bonds, or both.

Aryl

The term "aryl" as used herein includes reference to a carbocyclyl as defined herein above that is aromatic. Aryl is often phenyl but also may be a polycyclic ring system, having two or more rings, e.g. naphthyl, fluorenyl, azulenyl, anthryl, phenanthryl etc.

Hydrocarbylene, Carbocyclylene, Heterocyclylene, Alkylene and Arylene

The terms "hydrocarbylene", "carbocyclylene", "heterocyclylene", "alkylene" and "arylene" as used herein, refer to diradicals derived from the corresponding hydrocarbon, carbocycle, heterocycle, alkane (or alkene or alkyne, when insaturated) or arene, and are essentially analogous to the corresponding monoradicals defined herein, except for being diradicals.

The present invention is concerned with a process for converting tertiary phosphine oxides to the corresponding tertiary phosphines, numerous embodiments related to said conversion, as well as various uses for this highly efficient, simple, environmentally friendly, and scalable process.

The process comprises reacting a tertiary phosphine oxide, which it is desirable to reduce into the corresponding phosphine, with a reducing tertiary phosphine, in the presence of a catalyst, which catalyzes the reduction of the tertiary phosphine oxide to be reduced. In the reaction, the reducing tertiary phosphine is oxidized to the corresponding tertiary phosphine oxide.

The Tertiary Phosphine Oxide and the Tertiary Phosphine Product

It should be realized that the process of the invention is not limited to any particular tertiary phosphine oxide and in fact, it is contemplated that any tertiary phosphine oxide may be reduced by the inventive process, by a proper selection of the reducing tertiary phosphine.

The tertiary phosphine oxide of the invention may contain any number of phosphine oxide functions to be reduced. For example, the tertiary phosphine oxide may contain from 1 to 3 e.g. 1 or 2 phosphine oxide functions. In one embodiment, the tertiary phosphine oxide contains 1 phosphine oxide function. In another embodiment, the tertiary phosphine oxide contains 2 phosphine oxide functions.

Furthermore, it is contemplated that the phosphine oxide may additionally contain other functional groups.

In one embodiment, the tertiary phosphine oxide is a compound of formula (I)

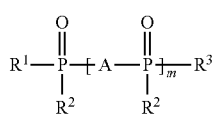

(I)

wherein $R^1$, $R^2$ and $R^3$ are each independently selected from the group comprising substituted or unsubstituted, branched or linear hydrocarbyl; and substituted or unsubstituted carbocyclyl or heterocyclyl;

A is a linking moiety; and m is an integer of from 0 to 2.

For example, each $R^1$, $R^2$ and $R^3$ may be independently selected from the group comprising $C_1$-$C_{20}$ alkyl, $C_6$-$C_{20}$ aryl-$C_0$-$C_{20}$ alkyl, $C_3$-$C_{20}$ cycloalkyl-$C_0$-$C_{20}$ alkyl, 5-20 membered heterocyclyl-$C_0$-$C_{20}$ alkyl; 5-20 membered heteroaryl-$C_0$-$C_{20}$ alkyl wherein any alkyl, cycloalkyl and heterocyclyl moiety may be saturated or unsaturated, any alkyl moiety may be branched or linear, and any alkyl, cycloalkyl, heterocyclyl, aryl and heteroaryl moiety is optionally substituted with one or several substituents.

In one embodiment, in a compound of formula (I), any $C_1$-$C_{20}$ alkyl may more particularly be a $C_1$-$C_{10}$ alkyl; any $C_0$-$C_{20}$ alkyl may more particularly be a $C_0$-$C_{10}$ alkyl; any $C_6$-$C_{20}$ aryl may more particularly be a $C_6$-$C_{14}$ aryl; any 5-20 membered heterocyclyl may more particularly be a 5-14 membered heterocyclyl; and any 5-20 membered heteroaryl may more particularly be a 5-14 membered heteroaryl.

In one embodiment, in a compound of formula (I), any $C_1$-$C_{20}$ alkyl may more particularly be a $C_1$-$C_6$ alkyl; any $C_0$-$C_{20}$ alkyl may more particularly be a $C_0$-$C_6$ alkyl; any $C_6$-$C_{20}$ aryl may more particularly be a $C_6$-$C_{10}$ aryl; any 5-20 membered heterocyclyl may more partitularly be a 5-10 membered heterocyclyl; and any 5-20 membered heteroaryl may more particularly be a 5-10 membered heteroaryl.

For example, $R^1$, $R^2$ and $R^3$ may be each independently selected from the group comprising substituted or unsubstituted $C_6$-$C_{20}$ aryl-$C_0$-$C_{20}$ alkyl and $C_5$-$C_{20}$ heteroaryl-$C_0$-$C_{20}$ alkyl, e.g. substituted or unsubstituted $C_6$-$C_{20}$ aryl and $C_5$-$C_{20}$ heteroaryl, such as substituted or unsubstituted phenyl, naphthyl and furyl, in particular substituted or unsubstituted phenyl.

More particularly, $R^1$, $R^2$ and $R^3$ may be each independently selected from the group comprising substituted or unsubstituted $C_6$-$C_{20}$ aryl-$C_0$-$C_{20}$ alkyl, e.g. substituted or unsubstituted $C_6$-$C_{20}$ aryl, such as substituted or unsubstituted phenyl or naphthyl, in particular substituted or unsubstituted phenyl.

In one embodiment, $R^1$, $R^2$ and $R^3$ are all substituted or unsubstituted phenyl.

The integer m in formula (I) is an integer of from 0 to 2, e.g. 0 or 1.

In one embodiment, m in formula (I) is 0, in which case the tertiary phosphine oxide of the invention may be represented by the formula (I')

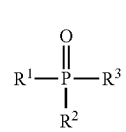

(I')

wherein $R^1$, $R^2$ and $R^3$ are as defined herein above.

In another embodiment, m in formula (I) is 1, and the tertiary phosphine oxide of the invention may then be represented by the formula (I")

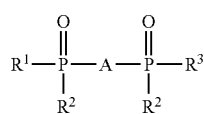

(I")

wherein $R^1$, $R^2$, $R^3$ and A are as defined herein above.

In one embodiment, in a compound of formula (I), $R^1$, $R^2$ and $R^3$ are all the same, e.g. all are substituted or unsubstituted phenyl.

Any reference made herein to a compound of formula (I), should be understood as a reference also to a compound of formula (I') or (I"), unless otherwise specified or apparent from the context.

The linking moiety A may be any diradical capable of attaching the two phosphorous atoms of the phosphine (oxide) functions to each other, through any number of intervening bonds. The linking moiety A may comprise substituted or unsubstituted hydrocarbylene or substituted or unsubstituted monocyclic or polycyclic carbocyclylene or heterocyclylene, and optionally one or several functional groups, such as ether or thioether function.

When m in formula (I) is more than 1, A is independently selected at each occurrence. In one embodiment, A is a polycyclic diradical, such as a diradical comprising 2 to 8 ring moieties, e.g. 2 to 6, or 2 to 4 ring moieties, wherein each ring moiety is independently selected from 5- or 6-membered, saturated or unsaturated, aromatic or non-aromatic carbocycles and hetercycles, and wherein the ring moieties are either fused to each other or attached to each other through one or several intervening bonds of e.g. covalent type or metallocene type, such as a covalent bond, an ether function, a thioether function, an optionally substituted alkylene group, e.g. a methylene or ethylene group, or a ferrocene type bond. In this embodiment, the two phosphine oxide functions preferably are attached to different ring moieties.

In another embodiment, A may be a substituted or unsubstituted hydrocarbylene, carbocyclylene, or heterocyclylene. The linking moiety A also may be a substituted or unsubstituted metallocenylene, i.e. a diradical derived from a metallocene, i.e. a compound with the general formula $(C_5H_5)_2M$ consisting of two cyclopentadienyl anions bound to a positively charged metal centre (M). As an example, A may be a substituted or unsubstituted ferrocenylene.

In one embodiment, A is an unsubstituted or substituted diradical selected from the group of substituted or unsubstituted, saturated or unsaturated, branched or linear $C_1$-$C_{20}$ alkylene, $C_3$-$C_{20}$ carbocyclylene, e.g. $C_6$-$C_{20}$ arylene, 5-20 membered heterocyclylene, e.g. 5-20 membered heteroarylene, $C_6$-$C_{40}$ bicyclylene, e.g. $C_{12}$-$C_{40}$ biarylene, 10-40 membered biheterocyclylene, e.g. 10-40 membered biheteroarylene, and $C_{10}$-$C_{30}$ ferrocenylene.

For example, A may be an unsubstituted or substituted diradical selected from the group of $C_6$-$C_{20}$ arylene, 5-20 membered heterocyclylene, 5-20 membered heteroarylene, $C_{12}$-$C_{40}$ biarylene, 10-40 membered biheterocyclylene, 10-40 membered biheteroarylene, and $C_{10}$-$C_{30}$ ferrocenylene.

In one embodiment, A is an unsubstituted or substituted diradical selected from the group of $C_{12}$-$C_{40}$ biarylene, 5-20 membered heterocyclylene and $C_{10}$-$C_{30}$ ferrocenylene, e.g. binaphthyl, such as 2,2'-binaphthyl; xanthenylene, e.g. 4,5-xanthenylene; and $(C_{10})$ferrocenylene, e.g. 1,1'-ferrocenylene.

Examples of tertiary phosphine oxides that may be reduced according to the invention are triphenylphosphine oxide, 2,2'-bis(diphenyloxyphosphino)-1,1'-binaphthyl, bis(2-(diphenyloxyphosphino)phenyl ether, 9,9-dimethyl-4,6-bis(diphenyloxyphosphino)-xanthene, 1,1'-bis(diphenyloxyphosphino) ferrocene, tris(4-chlorophenyl)phosphineoxide, bis(2-methylphenyl)phenylphosphineoxide, bis(2-methylphenyl) phenylphosphineoxide, or any of these compounds attached to a solid and/or polymeric support.

However, as noted herein above, the process of the invention very advantageously may be applied to essentially any tertiary phosphine oxide, and some examples of tertiary phosphines that may be prepared from the corresponding phosphine oxide by the reduction reaction according to the invention are:

di-(tert-butyl)phenylphosphine, di(1-methylbutyl)phenylphosphine, di(1,1-dimethylpropyl)phenylphosphine, di(1,1-dimethylbutyl)phenylphosphine, di-(tert-butyl)-2-methoxyphenylphosphine, di(1-methylbutyl)-2-methoxyphenylphosphine, di(1,1-dimethylpropyl)-2-methoxyphenylphosphine, di(1,1-dimethylbutyl)-2-methoxyphenylphosphine, bis(trimethylsilyl)-2-methoxyphenylphosphine, di-(tert-butyl)-4-methoxyphenylphosphine, di(1-methylbutyl)-4-methoxyphenylphosphine, di(1,1-dimethylpropyl)-4-methoxyphenylphosphine, di(1,1-dimethylbutyl)-4-methoxyphenylphosphine, di-(tert-butyl)-2,4-dimethoxyphenylphosphine, di(1-methylbutyl)-2,4-dimethoxyphenylphosphine, di(1,1-dimethylpropyl)-2,4-dimethoxyphenylphosphine, di(1,1-dimethylbutyl)-2,4-dimethoxyphenylphosphine, di-(tert-butyl)-2,4,6-trimethoxyphenylphosphine, di(1-methylbutyl)-2,4,6-trimethoxyphenylphosphine, di(1,1-dimethylpropyl)-2,4,6-trimethoxyphenylphosphine, di(1,1-dimethylbutyl)-2,4,6-tri-methoxyphenylphosphine, di-(tert-butyl)-2-methylphenylphosphine, di(1-methyl-butyl)-2-methylphenylphosphine, di(1,1-dimethyl-propyl)-2-methylphenylphosphine, di(1,1-dimethylbutyl)-2-methylphenyl-phosphine, di(tert-butyl)-4-methylphenylphosphine, di(1-methylbutyl)-4-methylphenylphosphine, di(1,1-dimethylpropyl)-4-methylphenylphosphine, di(1,1-dimethylbutyl)-4-methylphenylphosphine, di-(tert-butyl)-2,4-dimethylphenylphosphine, di(1-methylbutyl)-2,4-dimethylphenylphosphine, di(1,1-dimethylpropyl)-2,4-dimethylphenylphosphine, di(1,1-dimethylbutyl)-2,4-dimethylphenylphosphine, di-(tert-butyl)-2,4,6-trimethylphenylphosphine, di(1-methylbutyl)-2,4,6-trimethylphenylphosphine, di(1,1-dimethylpropyl)-2,4,6-trimethylphenylphosphine, di(1,1-dimethylbutyl)-2,4,6-trimethylphenylphosphine, di-(tert-butyl) pentafluorophenylphosphine, di(1-methylbutyl) pentafluorophenylphosphine, di(1,1-dimethylpropyl) pentafluorophenylphosphine, di(1,1-dimethylbutyl) pentafluorophenylphosphine, di-(tert-butyl)-2,4-difluorophenylphosphine, di(1-methylbutyl)-2,4-difluorophenylphosphine, di(1,1-dimethylpropyl)-2,4-difluorophenylphosphine, di(1,1-dimethylbutyl)-2,4-difluorophenylphosphine, di-(tert-butyl)-3,5-difluorophenylphosphine, di(1-methylbutyl)-3,5-difluorophenylphosphine, di(1,1-dimethylpropyl)-3,5-difluorophenylphosphine, di(1,1-dimethylbutyl)-3,5-difluorophenylphosphine, di(tert-butyl)-4-fluorophenylphosphine, di(1-methylbutyl)-4-fluorophenylphosphine, di(1,1-dimethylpropyl)-4-fluorophenylphosphine, di(1,1-dimethylbutyl)-4-fluorophenylphosphine, di(1,2-dimethylbutyl)-4- fluorophenylphosphine, di(tert-butyl)-4-chlorophenylphosphine, di(1-methylbutyl)-4-chlorophenylphosphine, di(1,1-dimethylpropyl)-4-chlorophenylphosphine, di(1,1-dimethylbutyl)-4-chlorophenylphosphine, di(tert-butyl)-4-bromophenylphosphine, di(1-methylbutyl)-4-bromophenylphosphine, di(1,1-dimethylpropyl)-4-bromophenylphosphine, di(1,1-dimethylbutyl)-4-bromophenylphosphine, di(tert-butyl)-4-(tert-butyl)phenylphosphine, di(1-methylbutyl)-4-(tert-butyl)phenylphosphine, di(1,1-dimethylpropyl)-4-(tert-butyl)phenylphosphine, di(1,1-dimethylbutyl)-4-(tert-butyl)phenylphosphine, bis(trimethylsilyl)-4-(tert-butyl)phenylphosphine, di(tert-butyl)-2,4,6-tri(tert-butyl)-phenylphosphine, di(1-methylbutyl)-2,4,6-tri(tert-butyl)phenylphosphine, di(1,1-dimethylpropyl)-2,4,6-tri(tert-butyl)phenylphosphine, di(1,1-dimethylbutyl)-2,4,6-tri(tert-butyl)-phenylphosphine, di-(tert-butyl)-4-trifluoromethylphenylphosphine, di(1-methylbutyl)-4-trifluoromethylphenylphosphine di(1,1-dimethylpropyl)-4-trifluoromethylphenylphosphine, di(1,1-dimethylbutyl)-4-trifluoromethylphenylphosphine, di-(tert-butyl)-3,5-bis(trifluoromethyl)phenylphosphine, di(1-methylbutyl)-3,5-bis(trifluoromethyl)phenylphosphine, di(1,1-dimethylpropyl)-3,5-bis(trifluoromethyl)phenylphosphine, di(1,1-dimethylbutyl)-3,5-bis(trifluoromethyl)phenylphosphine, di-(tert-butyl)-2-biphenylphosphine, di(1-methylbutyl)-2-biphenylphosphine, di(1,1-dimethylpropyl)-2-biphenylphosphine, di(1,1-dimethylbutyl)-2-biphenylphosphine, di(1,2-dimethylbutyl)-2-biphenylphosphine, bis(trimethylsilyl)-2-biphenylphosphine, di-(tert-butyl)-3-biphenylphosphine, di(1-methylbutyl)-3-biphenylphosphine, di(1,1-dimethylpropyl)-3-biphenylphosphine, di(1,1-dimethylbutyl)-3-biphenylphosphine, di-(tert-butyl)-1-naphthylphosphine, di(1-methylbutyl)-1-naphthylphosphine, di(1,1-dimethylpropyl)-1-naphthylphosphine, di(1,1-dimethylbutyl)-1-naphthylphosphine, di-(tert-butyl)-2-naphthylphosphine, di(1-methylbutyl)-2-naphthylphosphine, di(1,1-dimethylpropyl)-2-naphthylphosphine, di(1,1-dimethylbutyl)-2-naphthylphosphine, di-(tert-butyl)-5-acenaphthylphosphine, di(1-methylbutyl)-5-acenaphthylphosphine, di(1,1-dimethylpropyl)-5-acenaphthylphosphine, di(1,1-dimethylbutyl)-5-acenaphthylphosphine, di-(tert-butyl)-9-fluorenylphosphine, di(1-methylbutyl)-9-fluorenylphosphine, di(1,1-dimethylpropyl)-9-fluorenylphosphine, di(1,1-dimethylbutyl)-9-fluorenylphosphine, di-(tert-butyl)-9-anthracenylphosphine, di(1-methylbutyl)-9-anthracenylphosphine, di(1,1-dimethylpropyl)-9-anthracenylphosphine, di(1,1-dimethylbutyl)-9-anthracenylphosphine, di-(tert-butyl)-9-phenanthrylphosphine, di(1-methylbutyl)-9-phenanthrylphosphine, di(1,1-dimethylpropyl)-9-phenanthrylphosphine, di(1,1-dimethylbutyl)-9-phenanthrylphosphine, di-(tert-butyl)-1-pyrenylphosphine, di(1-methylbutyl)-1-pyrenylphosphine, di(1,1-dimethylpropyl)-1-pyrenylphosphine, di(1,1-dimethylbutyl)-1-pyrenylphosphine, 1,2-bis(di-tert-butylphosphino)benzene, 1,2-, 1,2-bis(di-1-methylbutyl-phosphino)benzene, 1,2-bis[di(1,1-dimethylpropyl)phosphino]benzene, 1,2-bis[bis(1,1-dimethylbutyl)-phosphino]benzene, 1,2-bis[bis(trimethylsilyl)methylphosphino)benzene, 1,3-bis(di-tert-butylphosphino)benzene, 1,3-bis[bis-(trimethylsilylphosphino)]benzene, 1,3-bis(di-1-methylbutylphosphino)benzene, 1,3-bis-[di(1,1-dimethylpropyl)phosphino]benzene, 1,3-bis[bis(1,1-dimethylbutyl)phosphino]benzene, 1,3-bis-[bis(trimethylsilyl)methylphosphino)benzene, 1,4-bis(di-tert-butyl-phosphino)benzene, 1,4-bis(di-1-methylbutylphosphino)benzene, 1,4-bis[di(1,1-dimethylpropyl)phosphino]-benzene, 1,4-bis[bis(1,1-dimethylbutyl)phosphino]-benzene, 1,4-bis[bis(trimethylsilyl)-methylphosphino) benzene. 1,4-bis(di-tert-butyl-phosphino)-cyclohexane, 1,4-bis(di-1-methylbutylphosphino)cyclohexane, 1,4-bis[di(1,1-di-methylpropyl)phosphino]-cyclohexane, 1,4-bis[bis(1,1-dimethylbutyl)phosphino]-cyclohexane, 1,4-bis[bis(trimethylsilyl)-methylphosphino)cyclohexane, 1,1'-bis(di-tert-butylphosphino)ferrocene, 1,1'-bis(di-1-methylbutylphosphino)ferrocene, 1,1'-bis[di(1,1-dimethylpropyl)phosphino]ferrocene, 1,1'-bis[bis(trimethylsilyl)methylphosphino)ferrocene, 1,2-bis(di-tert-butylphosphino)-ferrocene, 1,2-bis(di-1-methylbutylphosphino)ferrocene, 1,2-bis[di(1,1-dimethylpropyl)phosphino]ferrocene, 1,2-bis[bis(1,1-dimethylbutyl)phosphino]ferrocene, 1,2-bis-[bis(trimethylsilyl)methylphosphino)ferrocene, tri-tert-butylphosphine, trineopentylphosphine, tris(trimethylsilyl)phosphine, tri(1-methylbutyl)phosphine, tri(1-ethylpropyl)phosphine, tri(1,1-dimethylpropyl)phosphine, tris(1,2-dimethylpropyl)phosphine, tri(1-methylpentyl)phosphine, tris(1,1-dimethylbutyl)phosphine, tris(1,2-dimethylbutyl)phosphine, tris(1,3-dimethylbutyl)phosphine, tri(1-ethylbutyl)phosphine, tris(1,1,2-trimethylpropyl)phosphine, tris(1,2,2-trimethylpropyl)phosphine, tri(1-ethyl-1-methylpropyl)phosphine, tris[(trimethylsilyl)methyl]phosphine, tri(tert-butyl)phosphine, trineopentylphosphine, 2,2'-bis[bis(3,5-dimethylphenyl)phosphino]-1,1'-binaphthyl, 2,2'-bis[bis(4-methoxyphenyl)phosphino]-1,1'-binaphthyl, 2,2'-bis[bis(4-dimethylaminophenyl)phosphino]-1,1'-binaphthyl, 2,2'-bis[bis(4-fluorophenyl)phosphino]-1,1'-binaphthyl, 2,2'-bis[bis(3,5-di-tert-butyl-4-methoxyphenyl)phosphino]-1,1'-binaphthyl, 2,2'-bis(diphenylphosphino)-1,1'-binaphthyl, 2,2'-bis[bis(2-methylphenyl)phosphino]-1,1'-binaphthyl, 2,2'-bis[bis(3-methylphenyl)phosphino]-1,1'-binaphthyl, 2,2'-bis[bis(4-methyl-phenyl)phosphino]-1,1'-binaphthyl, 2,2'-bis[bis(4-tert-butylphenyl)phosphino]-1,1'-binaphthyl, 2,2'-bis[bis(3,5-di-tert-butylphenyl)phosphino]-1,1'-binaphthyl, 2,2'-bis[bis(4-methoxy-3,5-dimethylphenyl)phosphino]-1,1'-binaphthyl, 2,2'-bis[bis(4-chlorophenyl)phosphino]-1,1'-binaphthyl, 2,2'-bis[bis(1,3-benzodioxol-5-yl)phosphino]-1,1'-binaphthyl, 2,2'-bis[bis(2-naphthyl)phosphino]-1,1'-binaphthyl, 2,2'-bis(diphenylphosphino)-6,6'-diphenyl-1,1'-binaphthyl, 2,2'-bis(diphenylphosphino)-7,7'-dimethoxy-1,1'-binaphthyl, and any of these phosphines attached to a solid and/or polymeric support, e.g. 4-diphenylphosphinomethyl on polystyrene resin, and JandaJel™-triphenylphosphine (JandaJel™ is a polystyrene resin available from Sigma-Aldrich Co.), and the like.

It should be realized that the compounds of the invention may include one or several atoms having an (R) form and (S) form, in which case all forms and combinations thereof are contemplated as included within the scope of the invention, as well as any mixture of any isomeres.

The Reducing Tertiary Phosphine

The reducing tertiary phosphine may contain one or several tertiary phosphine functions and the phosphorus atom of each phosphine function may be linked to groups selected from substituted or unsubstituted, branched or linear hydrocarbyl; and substituted or unsubstituted carbocyclyl or heterocyclyl, as defined herein above.

For example, the reducing tertiary phosphine may contain from 1 to 3 phosphine functions. In one embodiment, the reducing tertiary phosphine contains 1 or 2 phosphine functions. In one particular embodiment, the reducing tertiary phosphine contains 1 phosphine function.

Furthermore, it is contemplated that the reducing tertiary phosphine may additionally contain other functional groups.

In one embodiment, the reducing tertiary phosphine is represented by the formula (II)

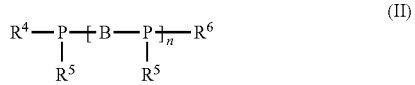

(II)

wherein $R^4$, $R^5$ and $R^6$ are each independently selected from the group comprising substituted or unsubstituted, branched or linear hydrocarbyl; and substituted or unsubstituted, aliphatic or aromatic carbocyclyl or heterocyclyl;

B is a linking moiety; and n is an integer of from 0 to 2, e.g. 0 or 1.

For example, $R^4$, $R^5$ and $R^6$ may be selected from the group comprising substituted or unsubstituted, branched or linear $C_1$-$C_{20}$ hydrocarbyl, e.g. $C_1$-$C_{10}$ hydrocarbyl, e.g. $C_1$-$C_6$ hydrocarbyl; and substituted or unsubstituted, aliphatic or aromatic $C_3$-$C_{20}$ carbocyclyl, e.g. $C_3$-$C_{10}$ carbocyclyl, or $C_3$-$C_6$ carbocyclyl, or 5-20 membered heterocyclyl, e.g. 5-10 membered heterocyclyl, or 5-6 membered heterocyclyl.

In one embodiment, $R^4$, $R^5$ and $R^6$ are independently selected from the group comprising substituted or unsubstituted, branched or linear $C_1$-$C_{20}$ hydrocarbyl, e.g. $C_1$-$C_{10}$ hydrocarbyl, e.g. $C_1$-$C_6$ hydrocarbyl; and substituted or unsubstituted, aliphatic $C_3$-$C_{20}$ carbocyclyl, e.g. $C_3$-$C_{10}$ carbocyclyl, or $C_3$-$C_6$ carbocyclyl. For example, any hydrocarbyl moiety may be an alkyl and any carbocyclyl moiety may be a cycloalkyl.

In one embodiment, $R^4$, $R^5$ and $R^6$ are all the same, although they may equally well be different from each other.

The number of phosphine functions in the compound of formula (II) suitably may range from 1 to 3, i.e. the integer n in formula (II) is from 0 to 2. In one embodiment, n in formula (II) is 0, in which case the reducing tertiary phosphine of the invention may be represented by the formula (II')

(II?)

wherein $R^4$, $R^5$ and $R^6$ are as defined herein above.

In another embodiment, n in formula (II) is 1 or 2.

In one embodiment, in a compound of formula (II), $R^4$, $R^5$ and $R^6$ are all the same, e.g. all are substituted or unsubstituted $C_1$-$C_6$ alkyl or $C_3$-$C_6$ cycloalkyl.

The linking moiety B may be any diradical capable of attaching the two phosphorous atoms of the phosphine (oxide) functions to each other, through any number of intervening bonds. The linking moiety B may comprise substituted or unsubstituted hydrocarbylene, monocyclic or polycyclic carbocyclylene or heterocyclylene, and optionally one or several functional groups, such as ether or thioether function.

When n in formula (II) is more than 1, B is independently selected at each occurrence.

In one embodiment, B is a polycyclic diradical, such as a diradical comprising 2 to 8 ring moieties, e.g. 2 to 6, or 2 to 4 ring moieties, wherein each ring moiety is independently selected from 5- or 6-membered, saturated or unsaturated, aromatic or non-aromatic, carbocycles and heterocycles, and wherein the ring moieties are either fused to each other or attached to each other through one or several intervening bonds of e.g. covalent type or metallocene type, such as a covalent bond, an ether function, a thioether function, an optionally substituted alkylene group, e.g. a methylene or ethylene group, or a ferrocene type bond. In this embodiment, the two phosphine oxide functions preferably are attached to different ring moieties.

In another embodiment, B may be a substituted or unsubstituted hydrocarbylene, carbocyclylene, or heterocyclylene. The linking moiety B also may be a substituted or unsubstituted metallocenylene, i.e. a diradical derived from a metallocene, i.e. a compound with the general formula $(C_5H_5)_2M$ consisting of two cyclopentadienyl anions bound to a positively charged metal centre (M). As an example, B may be a substituted or unsubstituted ferrocenylene.

In one embodiment, B is an unsubstituted or substituted diradical selected from the group of substituted or unsubstituted, saturated or unsaturated, branched or linear $C_1$-$C_{20}$ alkylene, $C_3$-$C_{20}$ carbocyclylene, e.g. $C_6$-$C_{20}$ arylene, 5-20 membered heterocyclylene, e.g. 5-20 membered heteroarylene, $C_6$-$C_{40}$ bicyclylene, e.g. $C_{12}$-$C_{40}$ biarylene, 10-40 membered biheterocyclylene, e.g. 10-40 membered biheteroarylene, and $C_{10}$-$C_{30}$ ferrocenylene.

For example, B may be an unsubstituted or substituted diradical selected from the group of $C_6$-$C_{20}$ arylene, 5-20 membered heterocyclylene, 5-20 membered heteroarylene, $C_{12}$-$C_{40}$ biarylene, 10-40 membered biheterocyclylene, 10-40 membered biheteroarylene, and $C_{10}$-$C_{30}$ ferrocenylene.

In one embodiment, B may is an unsubstituted or substituted diradical selected from the group of $C_{12}$-$C_{40}$ biarylene, 5-20 membered heterocyclylene and $C_{10}$-$C_{30}$ ferrocenylene, e.g. binaphthyl, such as 2,2'-binaphthyl; xanthenylene, e.g. 4,5-xanthenylene; and $(C_{10})$ ferrocenylene, e.g. 1,1'-ferrocenylene.

The basicity of the reducing tertiary phosphine preferably is greater than the basicity of the product phosphine. This is because a more basic phosphine is more easily oxidized than a less basic phosphine. However, the person of ordinary skill in the art will realize that the reaction according to the invention may additionally be driven in the desired direction e.g. by addition of an excess of the reducing tertiary phosphine to the reaction mixture.

As used herein, the term "basicity" essentially refers to the capability of the phosphine of donating electron pairs, i.e. of acting as a Lewis base; the electron pairs involved being those of the phosphine-phosphorus.

The basicity of the reducing phosphine mainly is governed by the groups linked to the phosphine function(s), i.e. mainly the groups $R^4$, $R^5$ and $R^6$ in the formula (II). For example, compounds of formula (II) wherein $R^4$, $R^5$ and $R^6$ are selected from $C_1$-$C_6$ alkyl and $C_3$-$C_6$ cycloalkyl, such as tri-tert-butylphosphine and tricyclopropylphosphine, are quite basic compounds and as such they are advantageous as reducing tertiary phosphines for use in a process according to the invention.

The tertiary reducing phosphine thus preferably is selected so as to be a stronger base than the tertiary phosphine oxide reduction product. Additional parameters for selecting the tertiary reducing phosphine may be e.g. ease of handling, availability and low cost.

The oxidation product of the reducing tertiary phosphine normally is considered a side product of the process. However, it should be realized that, if so desired, also this oxidation product may be collected and e.g. recycled through reduction or used in any other way.

Non-limiting examples of reducing tertiary phosphine suitable for the process of the present invention may be selected from the group comprising tributylphosphine, triethylphosphine, trimethylphosphine, tricyclohexylphosphine, tri-tert-butylphosphine, triphenylphosphine and other similar phosphines.

The reducing tertiary phosphine preferably is present in an amount corresponding to at least 1 molar equivalent phosphine-phosphorus of the reducing tertiary phosphine to the phosphine oxide-phosphorus of the tertiary phosphine oxide. For example, the reducing tertiary phosphine may suitably be present in an amount such as the molar ratio of the phosphine function(s) of the reducing tertiary phosphine to the phosphine oxide function(s) of the tertiary phosphine oxide to be reduced is from about 1 to about 10, e.g. from about 1.2 to about 5, e.g. about 1.5 to about 2.5, or approximately 2.

In one embodiment, the reducing tertiary phosphine is present in excess, compared to the phosphine oxide. In this embodiment, the reducing tertiary phosphine may suitably be present in an amount such as the molar ratio of the phosphine function(s) of the reducing tertiary phosphine to the phosphine oxide function(s) of the tertiary phosphine oxide to be reduced is from about 2 to about 10, e.g. from about 3 to about 8, or about 4 to about 6.

In one embodiment, the reducing tertiary phosphine is attached to a solid support. In this embodiment, the reducing tertiary phosphine may be regenerated after use, e.g. by reacting it with a reduction agent, such as a reducing tertiary phosphine, which may be more basic than the reducing tertiary phosphine attached to the solid phase or which is added in an excess to the reaction medium containing the solid phase with the attached reducing phosphine to be regenerated.

The Catalyst

In accordance with the invention, the catalyst can be any type of chemical species capable of catalyzing the reaction of the invention. Preferably the catalyst comprises at least one halogen atom. The catalyst may inter alia be selected from the group comprising fluorine ($F_2$), chlorine ($Cl_2$), bromine ($Br_2$), iodine ($I_2$), e.g. $I_2$ and $Br_2$; haloalkanes, in particular tetrahalomethanes, such as tetrachloromethane, tetrabromomethane, tetraiodomethane, tetrafluoromethane, e.g. $CCl_4$; phosphine dihalides, e.g. tertiary phosphine dihalides, such as triphenylphosphine dichloride, triphenylphosphine dibromide, triphenylphosphine diiodide, triphenylphosphine difluoride, e.g. triphenylphosphine dichloride, and/or any trialkyl, cycloalkyl or aryl analogues thereof The catalyst only needs to be present in catalytic amounts, but, since spurious water present in reagents and in solvents may consume catalyst, the optimal catalyst loading may be e.g. 0.02-0.5 molar equivalents of the tertiary phosphine oxide to be reduced, in particular 0.05-0.2 molar equivalents, e.g. 0.08-0.12 molar equivalents and suitably approximately 0.1 molar equivalents. In fact, increasing the amount of catalyst above the indicated ranges does not appear to have any significant effect on the reaction. However, depending on the utilized catalyst, higher/lower molar equivalents may be relevant, and increasing/decreasing the amount of catalyst is thus also within the scope of the present invention.

The catalyst may be present in any physical form, but suitable forms known to a person skilled in the art for a particular combination of reagents and/or reaction conditions are naturally preferable.

Without wishing to be bound by any particular theory, it is surmised that the reaction mechanism of the process of the present invention is reliant on an initial interaction between the catalyst and the reducing tertiary phosphine, possibly leading to an intermediary complex formed between at least certain components of these two molecules. Subsequently, the tertiary phosphine oxide is reduced into its corresponding tertiary phosphine, a reaction facilitated by the intermediary complex generated from the catalyst and the reducing tertiary phosphine. Theoretically, the process of the present invention thus results in, in total, reduction of the tertiary phosphine oxide into the corresponding tertiary phosphine, oxidation of the reducing tertiary phosphine into the corresponding tertiary phosphine oxide, as well as regeneration of the catalyst.

The Reaction Medium

The process of converting the tertiary phosphine oxide into the corresponding phosphine may be performed under solvent-free conditions, in order to further reduce the environmental impact of the process. The process of the present invention has, by virtue of the selection of reagents and conditions under which the reaction is taking place, a remarkably low environmental impact, but the possibility to utilize solvent-free reaction conditions further optimizes the eco-friendly characteristics of the present invention. However, the process may also be carried out in anhydrous aprotic solvent(s), such as for instance toluene, hexane, tetrahydrofuran (THF), acetonitrile, diethylether, propionitrile, benzonitrile, ethyl acetate and mixtures of these, e.g. tetrahydrofuran, acetonitrile, diethylether, propionitrile, toluene, ethyl acetate and mixtures of these. A preferable solvent for the process of the present invention may be selected from the group comprising acetonitrile and a 1 to 1 mixture of acetonitrile and THF.

The order of addition of the reaction constituents has no effect on the process, with the implication that obstacles associated with scale-up and handling can be minimized. Further, as a result of the advantageous characteristics of the present invention, the process can be carried out in virtually any type of reaction vessel, additionally increasing the versatility, specifically from an industrial perspective, of the invention.

The process of the present invention is, as mentioned herein above, associated with numerous advantages pertaining to inexpensiveness, low environmental impact, scalability, and ease of handling. Further advantageous aspects of the invention relate for instance to the fact that the process may be carried out at any temperature, most conveniently at ambient temperature, and that the concentration of the reaction mixture does not affect the process. Additionally, the process is very mild and thus highly suitable for sensitive reaction systems. For instance, the process of the present invention is ideally suitable for use in the reduction of tertiary phosphine oxides attached to a polymeric carrier or backbone, so as to regenerate the tertiary phosphine attached to the polymeric carrier or backbone. For instance the process of the invention may be used in the regeneration of triphenylphosphine on polystyrene. Such uses, and additional uses for regenerating tertiary phosphines attached to solid support, imply that the regenerated agents can be used repeatedly, resulting in minimized costs and optimized processes, especially for applications on a more industrial scale.

The Solid Support

As noted herein above, either the tertiary phosphine oxide or the reducing phosphine may be attached to a solid support. An example of such a solid support is a polystyrene material, such as sold under the trade name JandaJel™, by Sigma-Aldrich Co. Other possible solid phase supports are e.g. silica gel, Ring-Opening Olefin Metathesis Polymerization (ROMP) gel etc.

The person of ordinary skill in the art will now of various other possible solid supports, such as those described e.g. in U.S. Pat. No. 7,491,779 to Steinke, et al., the contents of which are incorporated by reference.

The attachment to the solid support is achieved through use of well-known chemistry for bonding compounds of the present type to a solid phase, and the skilled person is well able of selecting the proper reaction conditions and reactants. For example, triphenylphosphine attached to polystyrene may be prepared by copolymerizaion of diphenylstyrylphosphine and styrene or by copolymerization of diphenylphosphine and poly(4-bromostyrene).

Other Features of the Inventive Process

As may be noted from the Examples that will follow, which are intended for illustrative purposes only, and which are not to be construed as limiting the scope of the invention, the process of the invention very advantageously may be carried out at low reaction temperature, e.g. room temperature (e.g. 18-25° C.), and preferably is carried out under an inert atmosphere, e.g. a nitrogen atmosphere. Very advantageously, the reaction time may be kept very short, i.e. less than an hour, e.g. from 10 minutes to 30 minutes, giving a very high product yield of e.g. over 90 mole %, and up to 99 mole % or even an almost quantitative yield.

In one embodiment of the process of the invention, the tertiary phosphine oxide, the reducing tertiary phosphine and a catalyst are admixed, optionally in an anhydrous aprotic solvent. The mixture is stirred for the appropriate amount of time under an inert atmosphere. The reaction mixture suitably then is quenched, e.g. by addition of water.

The product may be extracted, purified and crystallized, e.g. by following the procedure described in the Examples. For example, in one embodiment, at the completion of the reaction, the reaction medium is diluted, if necessary, and washed with portions of a weak basic buffer solution, such as saturated $NaHCO_3$ The solution is dried, e.g. with $Na_2SO_4$, and filtered, whereafter the solvent is evaporated. The evaporation residue is redissolved in a hot solvent, e.g. EtOH, and made to crystallize, e.g. by keeping in a refrigerator. The product crystals then are filtered off, washed and dried. Of course, many variants of this procedure and modifications thereto will present themselves to the person of ordinary skill in the art, and all are considered to fall within the scope of the invention.

EXAMPLES

Example 1

100 mg (0.153 mmol) of 2,2'-Bis(diphenyloxyphosphino)-1,1'-binaphthyl were treated with 4 mg $I_2$ (16 μmol) and tributylphosphine 150 μl (0.6 mmol) in acetonitrile/THF (1:1 v/v) 1 mL. The mixture was stirred at room temperature for 10 minutes under nitrogen atmosphere before it was quenched with $H_2O$ (100 μL). The reaction mixture was diluted with ethyl acetate (10 mL) and was washed with portions of sat. $NaHCO_3$ (3×5 mL). The organic fraction was dried with $Na_2SO_4$, filtered and the solvent evaporated under vacuum. The resulting residue was recrystallized from EtOH, the resulting crystals were filtered, washed and dried in vacuum, giving 88 mg (0.141 mmol, 92%) of 2,2'-Bis(diphenylphosphino)-1,1'-binaphthyl (BINAP).

Example 2

100 mg (0.186 mmol) of Bis(2-(diphenyloxyphosphino) phenyl ether were treated with 5 mg $I_2$ (20 μmol) and tributylphosphine 185 μL (0.74 mmol) in acetonitrile/THF (1:1 v/v) 1 mL. The mixture was stirred at room temperature for 10 minutes under nitrogen atmosphere before it was quenched with $H_2O$ (100 μL). The reaction mixture was diluted with ethyl acetate (10 mL) and was washed with portions of sat. $NaHCO_3$ (3×5 mL). The organic fraction was dried with $Na_2SO_4$, filtered and the solvent evaporated under vacuum. The resulting residue was recrystallized from 1-propanol, the resulting crystals were filtered, washed and dried in vacuum, giving 94 mg (0.175 mmol, 94%) of Bis(2-(diphenylphosphino)phenyl ether (DPEphos).

Example 3

100 mg (0.164 mmol) of 9,9-Dimethyl-4,6-bis(diphenyloxyphosphino)xanthene were treated with 4 mg $I_2$ (16 μmol) and tributylphosphine 162 μL (0.65 mmol) in acetonitrile/THF (1:1 v/v) 1 mL. The mixture was stirred at room temperature for 10 minutes under nitrogen atmosphere before it was quenched with $H_2O$ (100 μL). The reaction mixture was diluted with ethyl acetate (10 mL) and was washed with portions of sat. $NaHCO_3$ (3×5 mL). The organic fraction was dried with $Na_2SO_4$, filtered and the solvent evaporated under vacuum. The resulting residue was recrystallized from 1-propanol, the resulting crystals were filtered, washed and dried in vacuum, giving 90 mg (0.156 mmol, 95%) of 9,9-Dimethyl-4,6-bis(diphenyloxyphosphino)xanthene (Xanthphos).

Example 4

100 mg (0.171 mmol) of 1,1'-Bis(diphenyloxyphosphino) ferrocene were treated with $I_2$ 4 mg (16 μmol) and tributylphosphine 170 μL (0.68 mmol) in acetonitrile/THF (1:1 v/v) 1 mL. The mixture was stirred at room temperature for 10 minutes under nitrogen atmosphere before it was quenched with $H_2O$ (100 μL). The reaction mixture was diluted with ethyl acetate (10 mL) and was washed with portions of sat. $NaHCO_3$ (3×5 mL). The organic fraction was dried with $Na_2SO_4$, filtered and the solvent evaporated under vacuum. The resulting residue was recrystallized from ethanol, the resulting crystals were filtered, washed and dried in vacuum, giving 89 mg (0.160 mmol, 94%) of 1,1'-Bis(diphenylphosphino)ferrocene (dppf).

Example 5

100 mg (0.262 mmol) of tris(4-chlorophenyl)phosphineoxide were treated with 6 mg $I_2$ (26 μmol) and tributylphosphine 130 μL (0.52 mmol) in acetonitrile/THF (1:1 v/v) 1 mL. The mixture was stirred at room temperature for 10 minutes under nitrogen atmosphere before it was quenched with $H_2O$ (100 μL). The reaction mixture was diluted with ethyl acetate (10 mL) and was washed with portions of sat. $NaHCO_3$ (3×5 mL). The organic fraction was dried with $Na_2SO_4$, filtered and the solvent evaporated under vacuum. The resulting residue was recrystallized from methanol (2 mL), the resulting crystals were filtered, washed and dried in vacuum, giving 95 mg (0.260 mmol, 99%) of tris(4-chlorophenyl)phosphine.

Example 6

100 mg (0.359 mmol) of triphenylphosphine oxide were treated with 9 mg $I_2$ (35 μmol) and tributylphosphine 180 μL (0.72 mmol) in acetonitrile/THF (1:1 v/v) 1 mL. The mixture was stirred at room temperature for 10 minutes under nitrogen atmosphere before it was quenched with $H_2O$ (100 μL). The reaction mixture was diluted with ethyl acetate (10 mL) and was washed with portions of sat. $NaHCO_3$ (3×5 mL). The organic fraction was dried with $Na_2SO_4$, filtered and the solvent evaporated under vacuum. The resulting residue was recrystallized from methanol, the resulting crystals were filtered, washed and dried in vacuum, giving 88 mg (0.334 mmol, 93%) of triphenylphosphine.

Example 7

3 g (0.12-0.18 mmol) of triphenylphosphine oxide polymer-bound on polystyrene support (31P NMR, bs, 24.5 ppm), were treated with I2 270 mg (1.07 mmol) and tributylphosphine 2 mL (8 mmol) in acetonitrile/THF (1:1 v/v) 12 mL. The mixture was stirred at room temperature for 4 hours under nitrogen atmosphere after which time the solid support was filtered off and washed with THF (10 ml). The solid support was analyzed by 31P NMR, no triphenylphosphine oxide signal could be seen only triphenylphosphine polymer-bound on polystyrene support (31P NMR, bs, −6.9 ppm).

Example 8

100 mg (0.359 mmol) of triphenylphosphine oxide were treated with 9 mg $I_2$ (35 μmol) and tributylphosphine 180 μL (0.72 mmol) in acetonitrile/toluene (1:1 v/v) 1 mL using the general procedure according to Example 6. Essentially the same results as in Example 6 were obtained.

Example 9

100 mg (0.359 mmol) of triphenylphosphine oxide were treated with 9 mg $I_2$ (35 μmol) and tributylphosphine 180 μL (0.72 mmol) in acetonitrile/diethylether (1:1 v/v) 1 mL using the general procedure according to Example 6. Essentially the same results as in Example 6 were obtained.

Example 10

100 mg (0.359 mmol) of triphenylphosphine oxide were treated with 9 mg $I_2$ (35 μmol) and tributylphosphine 180 μL (0.72 mmol) in acetonitrile/EtOAc (1:1 v/v) 1 mL using the general procedure according to Example 6. Essentially the same results as in Example 6 were obtained.

Example 11

100 mg (0.359 mmol) of triphenylphosphine oxide were treated with 9 mg $I_2$ (35 μmol) and triethylphosphine 106 μL (0.72 mmol) in acetonitrile 1 mL using the general procedure according to Example 6. Essentially the same results as in Example 6 were obtained.

Example 12

100 mg (0.431 mmol) of tri(2-furyl)phosphine oxide ($^{31}$P NMR, s, −15.4) were treated with $I_2$ 11 mg (43 μmol) and tributylphosphine 180 μL (0.70 mmol) in acetonitrile/THF (1:1 v/v) 2 mL for 19 hours at room temperature, which gave $^{31}$P NMR integrated conversion of tri(2-furyl)phosphine ($^{31}$P NMR, s, −76.5) in ca. 50%.

Example 13

100 mg (0.359 mmol) of triphenylphosphine oxide were treated with 9 mg $I_2$ (35 μmol) and tricyclohexylphosphine 202 mg (0.72 mmol) in acetonitrile 1 mL using the general procedure according to Example 6. Essentially the same results as in Example 6 were obtained.

Example 14

100 mg (0.359 mmol) of triphenylphosphine oxide were treated with 2 μl $Br_2$ (35 μmol) and tributylphosphine 180 μL (0.72 mmol) in acetonitrile 1 mL using the general procedure according to Example 6. Essentially the same results as in Example 6 were obtained.

Example 15

100 mg (0.359 mmol) of triphenylphosphine oxide were treated with 12 mg triphenylphosphine dichloride (35 μmol) and tributylphosphine 180 μL (0.72 mmol) in acetonitrile 1 mL for 48 hours at room temperature. Essentially the same results as in Example 6 were obtained.

Example 16

100 mg (0.359 mmol) of triphenylphosphine oxide were treated with 3 μl $CCl_4$ (35 μmol) and tributylphosphine 180 μL (0.72 mmol) in acetonitrile 1 mL using the general procedure according to Example 6. Essentially the same results as in Example 6 were obtained.

The invention claimed is:

1. A process for reducing a tertiary phosphine oxide to a corresponding tertiary phosphine, comprising reacting said tertiary phosphine oxide with a reducing tertiary phosphine, in the presence of a halogen catalyst selected from the group consisting of fluorine ($F_2$), chlorine ($Cl_2$), bromine ($Br_2$), iodine $I_2$), cyanuric chloride, halomethane, and phosphine dihalide.

2. The process according to claim 1, wherein
(i) the tertiary phosphine oxide is of formula (I)

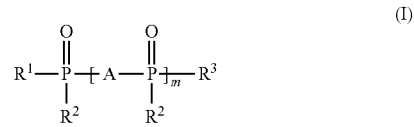

(I)

wherein, each of $R^1$, $R^2$ and $R^3$ is independently selected from the group consisting of substituted or unsubstituted, branched or linear hydrocarbyl; and substituted or unsubstituted carbocyclyl or heterocyclyl;
A is a linking moiety; and
m is an integer of from 0 to 2;
(ii) the corresponding tertiary phosphine is of formula (III)

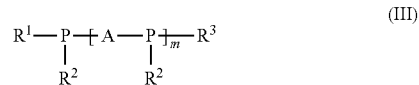

(III)

wherein $R^1$, $R^2$, $R^3$, A and m are as defined herein above; and
(iii) the reducing tertiary phosphine is of formula (II)

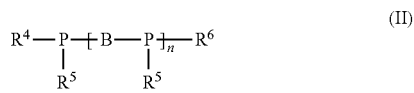

(II)

wherein, each of $R^4$, $R^5$ and $R^6$ is independently selected from the group consisting of substituted or unsubstituted, branched or linear hydrocarbyl; and substituted or unsubstituted, aliphatic or aromatic carbocyclyl or heterocyclyl;

B is a linking moiety; and n is an integer of from 0 to 2.

3. The process according to claim 2, wherein each of A and B is independently selected from substituted or unsubstituted hydrocarbylene, substituted or unsubstituted monocyclic or polycyclic carbocyclylene, substituted or unsubstituted monocyclic or polycyclic heterocyclylene, and substituted or unsubstituted metallocenylene.

4. The process according to claim 1, wherein the halogen catalyst is a tetrahalomethane.

5. The process according to claim 1, wherein the process is performed under solvent-free conditions or in an anhydrous aprotic solvent.

6. The process according to claim 5, wherein the anhydrous aprotic solvent is selected from the group consisting of tetrahydrofuran, acetonitrile, diethylether, propionitrile, toluene, ethyl acetate, and mixtures thereof.

7. The process according to claim 1, wherein the reducing tertiary phosphine is added to the reaction mixture at a molar ratio of the phosphine function(s) of the reducing tertiary phosphine to the phosphine oxide function(s) of the tertiary phosphine oxide of at least 1.

8. The process according to claim 1, wherein the basicity of the reducing tertiary phosphine is greater than the basicity of the product tertiary phosphine.

9. The process according to claim 1, wherein the tertiary phosphine oxide to be reduced is attached to a solid support.

10. The process according to claim 1, wherein the reducing tertiary phosphine is attached to a solid support.

11. The process according to claim 2, wherein the process is performed under solvent-free conditions or in an anhydrous aprotic solvent.

12. The process according to claim 3, wherein the process is performed under solvent-free conditions or in an anhydrous aprotic solvent.

13. The process according to claim 4, wherein the process is performed under solvent-free conditions or in an anhydrous aprotic solvent.

14. The process according to claim 1, wherein the halogen catalyst is $Br_2$ or $I_2$.

15. The process according to claim 4, wherein the tetrahalomethane is selected from the group consisting of tetrachloromethane, tetrabromomethane, tetraiodomethane, and tetrafluoromethane.

16. The process according to claim 1, wherein the halogen catalyst is tetrachloromethane.

17. The process according to claim 1, wherein the catalyst is a tertiary phosphine dihalide.

18. The process according to claim 17, wherein the tertiary phosphine dihalide is selected from the group consisting of triphenylphosphine dichloride, triphenylphosphine dibromide, triphenylphosphine diiodide, and triphenylphosphine difluoride.

19. The process according to claim 1, wherein the reaction is carried out at ambient temperatures.

* * * * *